United States Patent [19]
Bernardi et al.

[11] Patent Number: 4,675,404
[45] Date of Patent: Jun. 23, 1987

[54] 8-PYRIDAZINYLCARBAMOYL ERGOLINES

[75] Inventors: Luigi Bernardi; Aldemio Temperilli; Germano Bosisio; Gabriella Traquandi; Rosanna Eccel; Alessandro Rossi; Patricia Salvati, all of Milan, Italy

[73] Assignee: Farmitala Carlo Erba S.p.A., Milan, Italy

[21] Appl. No.: 885,315

[22] Filed: Jul. 14, 1986

Related U.S. Application Data

[63] Continuation of Ser. No. 578,306, Feb. 9, 1984, abandoned, which is a continuation of Ser. No. 398,894, Jul. 16, 1982, abandoned.

[30] Foreign Application Priority Data

Jul. 21, 1981 [GB] United Kingdom ............... 8122356
Mar. 31, 1982 [GB] United Kingdom ............... 8209544

[51] Int. Cl.$^4$ ................. C07D 457/02; C07D 457/06; A61K 31/48
[52] U.S. Cl. ..................... 544/238; 546/67; 546/69
[58] Field of Search .............. 546/67, 68, 69; 514/288; 544/238

[56] References Cited

U.S. PATENT DOCUMENTS

| | | | |
|---|---|---|---|
| 3,228,939 | 1/1966 | Bernardi et al. | 546/67 |
| 3,238,211 | 3/1966 | Camerino et al. | 424/261 |
| 3,880,856 | 4/1975 | Bach et al. | 424/261 |
| 3,904,634 | 9/1975 | Arcari et al. | 546/67 |
| 3,920,664 | 11/1975 | Clemens et al. | 546/68 |
| 4,035,501 | 7/1977 | Hauth | 546/69 |
| 4,101,552 | 7/1978 | Karacsony et al. | 546/69 |
| 4,166,911 | 9/1979 | Bernardi et al. | 546/67 |
| 4,182,883 | 1/1980 | Beran et al. | 546/67 |
| 4,526,892 | 7/1985 | Salvati et al. | 514/288 |

FOREIGN PATENT DOCUMENTS

| | | | |
|---|---|---|---|
| 790063 | 7/1968 | Canada | 546/69 |
| 2056437 | 3/1981 | European Pat. Off. | 546/67 |
| 4222781 | 5/1964 | Japan | 546/69 |
| 347197 | 8/1960 | Switzerland | 546/69 |
| 392532 | 10/1965 | Switzerland | 546/69 |
| 2058746 | 4/1981 | United Kingdom | 544/346 |

OTHER PUBLICATIONS

Berde and Schild, Ergot Alkaloids and Related Compounds, Springer-Verlag, New York, 1978.

Primary Examiner—Donald G. Daus
Assistant Examiner—G. Hendricks
Attorney, Agent, or Firm—Oblon, Fisher, Spivak, McClelland & Maier

[57] ABSTRACT

Ergoline derivatives of formula:

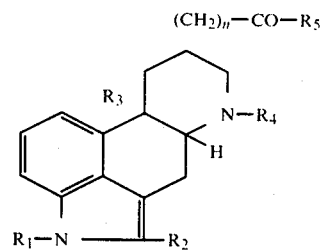

wherein $n=0,1,2$; $R_1=H$, $CH_3$; $R_2=H$, $CH_3$, halogen; $R_3=H$, $OCH_3$; $R_4=$hydrocarbon group and $R_5$ is a residue of general formula II, III, IV, V, VI, VII:

wherein $R_6=H$, Cl, $OCH_3$, $NR_{11}R_{12}$, wherein $R_{11}$ and $R_{12}=H$, lower alkyl; phenyl or are bonded together to form a heterocyclic ring, $R_7$, $R_8$ and $R_9$ and $R_{10}=H$ or $C_1$-$C_3$ alkyl, with the proviso that if $R_5$ is of formula II and $R_2=R_7=R_8=H$, then $R_4$ is not methyl or n is not 0.

Pharmaceutically acceptable acid addition salts are also provided. A method for their preparation is also provided.

The compounds have anti-depressive, anti-hypertensive and antiprolactin activity.

3 Claims, No Drawings

8-PYRIDAZINYLCARBAMOYL ERGOLINES

This application is a continuation of application Ser. No. 578,306, filed Feb. 9, 1984, now abandoned, which is a continuation of Ser. No. 398,894, filed 7/16/1982, now abandoned.

This invention relates to ergoline derivatives, to processes for their preparation, and to pharmaceutical compositions containing them.

More particularly, this invention relates to ergoline derivatives having the general formula I:

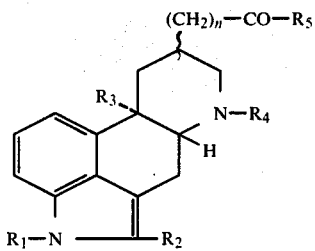

wherein n is 0, 1 or 2, $R_1$ represents a hydrogen atom or a methyl group, $R_2$ represents a hydrogen or halogen atom or a methyl group, $R_3$ represents a hydrogen atom or a methoxy group, $R_4$ represents a hydrocarbon group having from 1 to 4 carbon atoms, and $R_5$ is a residue of the general formula II, III, IV, V, VI, VII or VIII:

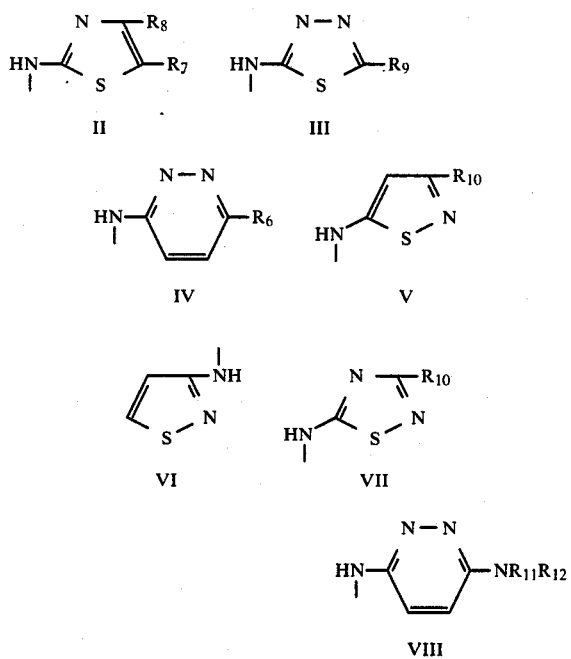

wherein $R_6$ represents a hydrogen or chlorine atom or a methoxy group, and each of $R_7$, $R_8$ and $R_9$ independently represents a hydrogen atom or an alkyl group having from 1 to 3 carbon atoms, with the proviso that if $R_5$ represents a residue of the general formula II and $R_2$, $R_7$ and $R_8$ all represent hydrogen atoms then either $R_4$ does not represent a methyl group or n is not 0, or the substituent on $C_8$ is not in $\beta$ configuration, $R_{10}$ represents a hydrogen atom or an alkyl group having from 1 to 3 carbon atoms, and either each of $R_{11}$ and $R_{12}$ independently represents a hydrogen atom, a $C_1$ to $C_4$ alkyl group or a phenyl group, or $R_{11}$ and $R_{12}$ together with the nitrogen atom to which they are bonded form a heterocyclic ring, and further provides pharmaceutically acceptable salts of such ergoline derivatives.

Although in the general formula thr term "halogen" should be construed as preferably encompassing chlorine and bromine atom, nevertheless, the term "halogen" also encompasses the fluorine atom.

In the definition of $R_4$, a hydrocarbon group having from 1 to 4 carbon atoms is intended to include alkyl, cycloalkyl and unsaturated (both ethylenically and acetylenically) groups.

Representative groups include methyl, ethyl, n-propyl, isopropyl, butyl, t-butyl, isobutyl, methylcyclopropyl, allyl and propargyl.

When $R_{11}$ and $R_{12}$ together with the nitrogen atom to which they are bonded form a heterocyclic ring, this ring is preferably selected from the group consisting of pyrrolidine, piperidino, morpholino, pyrazole, imidazole and pyrrole.

The ergoline derivatives according to the invention may be prepared by the high-yield mixed anhydride method using the relatively stable and readily accessible mixed anhydride of the appropriate 8-carboxy-ergoline IX:

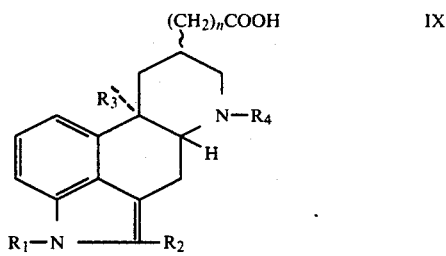

wherein n, $R_1$, $R_2$, $R_3$ and $R_4$ have the above meanings, with ethoxyformic acid.

The mixed ethoxyformic anhydride can be prepared by reacting the ergoline IX with ethyl chloroformate in a solvent such as tetrahydrofuran, dimethylformamide, or dioxan at 0° C. for 5-6 hours in the presence of an organic base such as triethylamine.

The so-obtained mixed anhydride may be converted into an ergoline derivative of the general formula I by reacting it with an amine $R_5$—H, wherein $R_5$ has the above meaning, at room temperature for a period of 2-24 hours. This process is also considered to be within the scope of the invention.

The crude product may be purified by crystallization, salt formation, or by chromatography on a column of neutral aluminum oxide.

The ergoline-8-carboxylic acids IX are known compounds or may be prepared by established procedures.

The ergoline derivatives according to the present invention and their pharmaceutically acceptable salts are useful antidepressant agents and they also display from moderate to good antiprolactinic activity and from moderate to good antihypertensive activity.

Accordingly, this invention also provides a pharmaceutical composition comprising an ergoline derivative having the general formula I or a pharmaceutically acceptable salt thereof in admixture with a pharmaceutically acceptable diluent or carrier.

The antidepressant activity of the ergoline derivatives according to the invention can be evaluated by antagonism to reserpine-induced blepharospasm and hypothermia.

As a compound disclosed in Belgian Patent No. 841,049 has a structural formula similar to that shown herein, applicants have ascertained by applicants' test that it prevents reserpine-induced blepharospasm and hypothermia with $ED_{50}$'s of 7 and 15 mg/kg p.o. Said compound is 1,6-dimethyl-8$\beta$-(2-thiazolyl-carbamoyl)-ergoline, and this was used as a reference standard drug, besides the tricyclic antidepressant imipramine, for the compounds of the present invention.

It has now been found that the products according to the present invention have a surprisingly higher activity as compared with the prior art compounds referred to above in preventing reserpine-induced symptoms with $ED_{50}$ falling in a dose range of from 0.2 to 5 mg/kg p.o., and with very low orientative acute toxicities. This is shown in the following table:

| Product of Example | Reserpine antagonism ($ED_{50}$, mg/kg p.o.) | | Orientative acute toxicity ($LD_{50}$, mg/kg, p.o.) |
| --- | --- | --- | --- |
| | Blepharospasm | hypothermia | |
| 7 | 0.5 | 0.6 | >300 |
| 6 | 2.5 | 4.0 | >300 |
| 4 | 0.2 | 0.6 | >300 |
| 16 | 1.0 | 1.7 | >800 |
| 5 | 3.6 | 4.5 | >600 |
| 10 | 3.5 | 3.1 | >600 |
| Imipramine | 8.1 | 18.2 | 200–400 |

The tests were performed in an air-conditioned room at a constant termperature of $19°\pm1°$ C. Randomized groups of male mice were respectively treated by gavage with appropriate screening doses (from a maximum of 25 mg/kg below) of the test compounds, suspended in the vehicle (Methocel 0.5%; 1 ml/100 g b.w.), or with the vehicle alone. One hour later the animals received an i.p. injection of reserpine (1.5 mg/kg; 1 ml/100 g b.w.), and one of the control groups the same volume of the vehicle alone (blank controls).

Three hours after pretreatments, i.e. two hours after reserpine or vehicle treatments, blepharospasm was evaluated in scores as proposed by Rubin et al. (J. Pharmacol. 120, 125 (1957)). Two hours after the above mentioned evaluation the rectal temperature of the animals was recorded by an appropriate probe connected to a digital thermometer (Ellab DU-3).

The following examples still further illustrate the invention.

EXAMPLE 1

6-methyl-8$\beta$-(6-chloro-3-pyridazinyl-carbamoyl)-ergoline (I:$R_1=R_2=R_3=H, R_4=CH_3, R_5=IV, R_6=Cl$)

A mixture of 15.02 g of 6-methyl-8$\beta$-carboxy-ergoline and 7 ml of triethylamine in 400 ml of anhydrous tetrahydrofuran was warmed at 50° C. for 1 hour. To the cooled suspension 5.34 ml of ethyl chloroformate in 20 ml of tetrahydrofuran were added slowly and the stirring was continued for 6 hours at 0° C. After filtration the clear solution treated with 7.12 g of 3-amino-6-chloro-pyridazine and left overnight at room temperature. The solution was concentrated under vacuum, dissolved in chloroform, and washed with potassium carbonate solution and then with water. The residue of the organic layer was chromatographed through a short column of alumina using chloroform as the eluting solvent. In this way 15 g of the title compound, m.p. 252°–254° C., were obtained.

EXAMPLES 2 to 38

Operating as in Example 1, the compounds in Table 2 below were prepared from the following ergoline derivatives and amines:

| | Examples |
| --- | --- |
| Ergoline derivative | |
| 6-methyl-8$\beta$-carboxy-ergoline | 2, 10, 27, 28, 32 |
| 1,6-dimethyl-10-methoxy-8$\beta$-carboxy-ergoline | 3, 11 |
| 2,6-dimethyl-8$\beta$-carboxy-ergoline | 4, 9, 16 |
| 1,6-dimethyl-8$\beta$-carboxy-ergoline | 12 |
| 6-allyl-8$\beta$-carboxy-ergoline | 5, 6, 14 |
| 6-propyl-8$\beta$-carboxy-ergoline | 7, 13 |
| 6-isopropyl-8$\beta$-carboxy-ergoline | 8, 15 |
| 6-methyl-8$\beta$-carboxymethyl-ergoline | 17, 19, 25, 29, 33, 35–38 |
| 6-methyl-8$\beta$-(2-carboxyethyl)-ergoline | 18, 20, 26, 30, 31, 34, 40 and 41 |
| 6-methyl-8$\alpha$-carboxy-ergoline | 21–23 |
| 1-methyl-6-propyl-8$\beta$-carboxy-ergoline | 24 |
| 2-bromo-6-methyl-8$\beta$-carboxymethyl-ergoline | 39 |
| Amine | |
| 3-amino-6-methoxy-pyridazine | 2, 36, 41 |
| 3-amino-6-chloro-pyridazine | 3–5, 19, 20, 23, 39 |
| 2-amino-thiazole | 6–9, 17, 18, 22, 24 |
| 2-amino-5-methyl-1,3,4-thiadiazole | 10–16, 21, 25, 26 |
| 5-amino-3-methyl-isothiazole | 27, 29, 30 |
| 3-amino-isothiazole | 28, 31 |
| 3-methyl-5-amino-1,2,4-thiadiazole | 32–34 |
| 3-aminopyridazine | 35, 40 |
| 3-amino-6-(1-pyrrolidinyl)-pyridazine | 37 |
| 3-amino-6-(1-pyrrolyl)-pyridazine | 38 |

| Example | Product | General Formula I | | | | | | m.p. (°C.) | yield (%) |
| --- | --- | --- | --- | --- | --- | --- | --- | --- | --- |
| | | n | $R_1$ | $R_2$ | $R_3$ | $R_4$ | $R_5$ | | |
| 2 | 6-methyl-8$\beta$-(6-methoxy-3-pyridazinyl-carbamoyl)-ergoline | 0 | H | H | H | $CH_3$ | IV, $R_6 = CH_3O$ | 273–274 | 65 |
| 3 | 1,6-dimethyl-10-methoxy-8$\beta$-(6-chloro-3-pyridazinyl-carbamoyl)-ergoline | 0 | $CH_3$ | H | $CH_3O$ | $CH_3$ | IV, $R_6 = Cl$ | 140–142 | 70 |
| 4 | 2,6-dimethyl-8$\beta$-(6-chloro-3-pyridazinyl-carbamoyl)-ergoline | 0 | H | $CH_3$ | H | $CH_3$ | IV, $R_6 = Cl$ | 278–280 | 75 |
| 5 | 6-allyl-8$\beta$-(6-chloro-3-pyridazinyl-carbamoyl)-ergoline | 0 | H | H | H | allyl | IV, $R_6 = Cl$ | 230–232 | 65 |
| 6 | 6-allyl-8$\beta$-(2-thiazolyl-carbamoyl)-ergoline | 0 | H | H | H | allyl | II, $R_7 = R_8 = H$ | 170–172 | 70 |
| 7 | 6-propyl-8$\beta$-(2-thiazolyl-carbamoyl)-ergoline | 0 | H | H | H | n-$C_3H_7$ | II, $R_7 = R_8 = H$ | 200–202 | 64 |
| 8 | 6-isopropyl-8$\beta$-(2-thiazolyl-carbamoyl)-ergoline | 0 | H | H | H | i-$C_3H_7$ | II, $R_7 = R_8 = H$ | 252–254 | 55 |
| 9 | 2,6-dimethyl-8$\beta$-(2-thiazolyl-carbamoyl)-ergoline | 0 | H | $CH_3$ | H | $CH_3$ | II, $R_7 = R_8 = H$ | 187–189 | 72 |
| 10 | 6-methyl-8$\beta$-[2-(5-methyl-1,3,4-thiadiazolyl)-carbamoyl]-ergoline | 0 | H | H | H | $CH_3$ | III, $R_9 = CH_3$ | 263–265 | 71 |

-continued

| Example | Product | n | $R_1$ | $R_2$ | $R_3$ | $R_4$ | $R_5$ | m.p. (°C.) | yield (%) |
|---|---|---|---|---|---|---|---|---|---|
| 11 | 1,6-dimethyl-10-methoxy-8β-[2-(5-methyl-1,3,4-thiadiazolyl)-carbamoyl]-ergoline | 0 | $CH_3$ | H | $CH_3O$ | $CH_3$ | III, $R_9 = CH_3$ | 218–220 | 68 |
| 12 | 1,6-dimethyl-8β-[2-(5-methyl-1,3,4-thiadiazolyl)-carbamoyl]-ergoline | 0 | $CH_3$ | H | H | $CH_3$ | III, $R_9 = CH_3$ | 152–154 | 80 |
| 13 | 6-propyl-8β-[2-(5-methyl-1,3,4-thiadiazolyl)-carbamoyl]-ergoline | 0 | H | H | H | n-$C_3H_7$ | III, $R_9 = CH_3$ | 202–204 | 70 |
| 14 | 6-allyl-8β-[2-(5-methyl-1,3,4-thiadiazolyl)-carbamoyl]-ergoline | 0 | H | H | H | allyl | III, $R_9 = CH_3$ | 156–158 | 67 |
| 15 | 6-isopropyl-8β-[2-(5-methyl-1,3,4-thiadiazolyl)-carbamoyl]-ergoline | 0 | H | H | H | i-$C_3H_7$ | III, $R_9 = CH_3$ | 194–196 | 73 |
| 16 | 2,6-dimethyl-8β-[2-(5-methyl-1,3,4-thiadiazolyl)-carbamoyl]-ergoline | 0 | H | $CH_3$ | H | $CH_3$ | III, $R_9 = CH_3$ | 258–260 | 70 |
| 17 | 6-methyl-8β-(2-thiazolyl-carbamoylmethyl)-ergoline | 1 | H | H | H | $CH_3$ | II, $R_7 = R_8 = H$ | 285–287 | 70 |
| 18 | 6-methyl-8β-[2-(2-thiazolyl-carbamoyl)-ethyl]-ergoline | 2 | H | H | H | $CH_3$ | II, $R_7 = R_8 = H$ | 246–248 | 72 |
| 19 | 6-methyl-8β-[2-(6-chloro-3-pyridazinyl-carbamoylmethyl)-ergoline | 1 | H | H | H | $CH_3$ | IV, $R_6 = Cl$ | 285–287 | 68 |
| 20 | 6-methyl-8β-[2-(6-chloro-3-pyridazinyl-carbamoyl)-ethyl]-ergoline | 2 | H | H | H | $CH_3$ | IV, $R_6 = Cl$ | 280–282 | 71 |
| 21 | 6-methyl-8β-[2-(5-methyl-1,3,4-thiadiazolyl)carbamoyl]-ergoline | 0 | H | H | H | $CH_3$ | III, $R_9 = CH_3$ | 293–5 | 69 |
| 22 | 6-methyl-8β-(2-thiazolyl-carbamoyl)ergoline | 0 | H | H | H | $CH_3$ | II, $R_7 = R_8 = H$ | 253–4 | 72 |
| 23 | 6-methyl-8β-(6-chloro-3-pyridazinyl-carbamoyl)ergoline | 0 | H | H | H | $CH_3$ | IV, $R_6 = Cl$ | 300 | 58 |
| 24 | 1-methyl-6-propyl-8β-(2-thiazolyl-carbamoyl)-ergoline | 0 | $CH_3$ | H | H | n-$C_3H_7$ | II, $R_7 = R_8 = H$ | 168–170 | 75 |
| 25 | 6-methyl-8β-[2-(5-methyl-1,3,4-thiadiazolyl)-carbamoylmethyl]-ergoline | 1 | H | H | H | $CH_3$ | III, $R_9 = CH_3$ | 300 | 68 |
| 26 | 6-methyl-8β-{2[2-(5-methyl-1,3,4-thiadiazolyl)-carbamoyl]-ethyl}-ergoline | 2 | H | H | H | $CH_3$ | III, $R_9 = CH_3$ | 275–277 | 71 |
| 27 | 6-methyl-8β-(3-methyl-5-isothiazolyl-carbamoyl)-ergoline | 0 | H | H | H | $CH_3$ | V, $R_{10} = CH_3$ | 174–175 | 62 |
| 28 | 6-methyl-8β-(3-isothiazolyl-carbamoyl)-ergoline | 0 | H | H | H | $CH_3$ | VI | 138–140 | 62 |
| 29 | 6-methyl-8β-(3-methyl-5-isothiazolyl-carbamoylmethyl)-ergoline | 1 | H | H | H | $CH_3$ | V, $R_{10} = CH_3$ | 138–140 | 65 |
| 30 | 6-methyl-8β-[2-(3-methyl-5-isothiazolyl-carbamoyl)-ethyl]-ergoline | 2 | H | H | H | $CH_3$ | V, $R_{10} = CH_3$ | 191–192 | 55 |
| 31 | 6-methyl-8β-[2-(3-isothiazolyl-carbamoyl)-ethyl]-ergoline | 2 | H | H | H | $CH_3$ | VI | 202–204 | 64 |
| 32 | 6-methyl-8β-[5-(3-methyl-1,2,4-thiadiazolyl)-carbamoyl]-ergoline | 0 | H | H | H | $CH_3$ | VII, $R_{10} = CH_3$ | 181–182 | 68 |
| 33 | 6-methyl-8β-[5-(3-methyl-1,2,4-thiadiazolyl)-carbamoylmethyl]-ergoline | 1 | H | H | H | $CH_3$ | VII, $R_{10} = CH_3$ | 243–245 | 60 |
| 34 | 6-methyl-8β-{2-[5-(3-methyl-1,2,4-thiadiazolyl)-carbamoyl]-ethyl}-ergoline | 2 | H | H | H | $CH_3$ | VII, $R_{10} = CH_3$ | 145–147 | 65 |
| 35 | 6-methyl-8β-(3-pyridazinyl-carbamoylmethyl)-ergoline | 1 | H | H | H | $CH_3$ | IV, $R_6 = H$ | 230–232 | 61 |
| 36 | 6-methyl-8β-(6-methoxy-3-pyridazinyl-carbamoylmethyl)-ergoline | 1 | H | H | H | $CH_3$ | IV, $R_6 = OCH_3$ | 258–260 | 71 |
| 37 | 6-methyl-8β-(6-pyrrolidinyl-3-pyridazinyl-carbamoylmethyl)-ergoline | 1 | H | H | H | $CH_3$ | VIII, $R_{11}$ and $R_{12}$ = 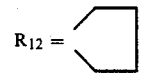 | 263–5 | 67 |
| 38 | 6-methyl-8β-[6-(pyrrolyl)-3-pyridazinyl-carbamoylmethyl]-ergoline | 1 | H | H | H | $CH_3$ | VIII, $R_{11}$ and $R_{12}$ = 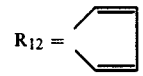 | 241–243 | 70 |
| 39 | 2-bromo-6-methyl-8β-[(6-chloro-3 pyridazinyl)carbamoylmethyl]-ergoline | 1 | H | Br | H | $CH_3$ | IV, $R_6 = Cl$ | 254–6 | 65 |
| 40 | 6-methyl-8β-[2(3-pyridazinyl-carbamoyl)ethyl]-ergoline | 2 | H | H | H | $CH_3$ | IV, $R_6 = H$ | 233–5 | 75 |
| 41 | 6-methyl-8β-[2(6-methoxy-3-pyridazinyl-carbamoyl)ethyl]ergoline | 2 | H | H | H | $CH_3$ | IV, $R_6 = OCH_3$ | 268–270 | 69 |

What is claimed is:

1. A compound which is 6-methyl-8β-(6-chloro-3-pyridazinyl-carbamoyl)-ergoline.

2. A compound which is 2,6-dimethyl-8β-(6-chloro-3-pyridazinyl-carbamoyl)-ergoline.

3. A compound which is 6-allyl-8β-(6-chloro-3-pyridazinyl-carbamoyl)-ergoline.

* * * * *